US010022087B2

(12) United States Patent
Holopainen et al.

(10) Patent No.: US 10,022,087 B2
(45) Date of Patent: Jul. 17, 2018

(54) SWIM STROKE COUNTER

(71) Applicants: Reima K. Holopainen, Zufikon (CH); Jari M. A. Tiira, Lenzburg (CH)

(72) Inventors: Reima K. Holopainen, Zufikon (CH); Jari M. A. Tiira, Lenzburg (CH)

(73) Assignee: Johnson Outdoors Inc., Racine, WI (US)

( * ) Notice: Subject to any disclaimer, the term of this patent is extended or adjusted under 35 U.S.C. 154(b) by 630 days.

(21) Appl. No.: 14/088,491

(22) Filed: Nov. 25, 2013

(65) Prior Publication Data
US 2014/0149066 A1    May 29, 2014

Related U.S. Application Data

(60) Provisional application No. 61/731,182, filed on Nov. 29, 2012.

(51) Int. Cl.
*A61B 5/11*    (2006.01)
*A61B 5/00*    (2006.01)
*G06K 9/00*    (2006.01)

(52) U.S. Cl.
CPC .......... *A61B 5/6829* (2013.01); *A61B 5/1126* (2013.01); *A61B 5/681* (2013.01); *G06K 9/00342* (2013.01); *A61B 2503/10* (2013.01); *A61B 2562/0247* (2013.01); *G06K 9/00523* (2013.01)

(58) Field of Classification Search
CPC ..... A63B 71/06; A63B 71/0686; A63B 24/00; A63B 24/0021; A63B 24/0003; A63B 24/0062; A63B 69/12; A61B 5/1126; A61B 5/681; A61B 2503/01; A61B 2562/0247; G06K 9/00342; G06K 9/00523; G01C 22/00; G07C 1/22
See application file for complete search history.

(56) References Cited

U.S. PATENT DOCUMENTS

| | | | |
|---|---|---|---|
| 4,530,105 A | 7/1985 | Rabinowitz | |
| 5,496,136 A * | 3/1996 | Egan | B63C 11/2245 405/186 |
| 5,592,401 A | 1/1997 | Kramer | |
| 5,663,897 A * | 9/1997 | Geiser | A63B 71/0686 441/56 |
| 5,685,722 A | 11/1997 | Taba | |
| 5,813,945 A | 9/1998 | Bernacki | |
| 5,930,741 A | 7/1999 | Kramer | |
| 6,086,379 A | 7/2000 | Pendergast et al. | |
| 6,122,960 A | 9/2000 | Hutchings et al. | |
| 6,154,140 A * | 11/2000 | Thorpe | B63C 11/02 340/573.6 |

(Continued)

FOREIGN PATENT DOCUMENTS

EP    1623743 A1    2/2006
GB    2 176 036 A    12/1986
(Continued)

*Primary Examiner* — Manuel L Barbee
(74) *Attorney, Agent, or Firm* — Reinhart Boerner Van Deuren P.C.

(57) ABSTRACT

A stroke counter and a method of analyzing strokes of swimmer are provided. The stroke counter and method use changes in pressure proximate the arms and legs of the swimmer to determine when the swimmer performs a swimming stroke using either the arms or legs.

26 Claims, 2 Drawing Sheets

(56) References Cited

U.S. PATENT DOCUMENTS

| | | |
|---|---|---|
| 6,305,221 B1 | 10/2001 | Hutchings et al. |
| 6,361,501 B1 | 3/2002 | Amano et al. |
| 6,450,922 B1 | 9/2002 | Henderson et al. |
| 6,710,713 B1 | 3/2004 | Russo |
| 6,745,069 B2 | 6/2004 | Nissilä et al. |
| 6,870,466 B2 | 3/2005 | Rust et al. |
| 6,901,031 B2 | 5/2005 | Murakoshi et al. |
| 6,955,542 B2 | 10/2005 | Roncalez et al. |
| 7,092,846 B2 | 8/2006 | Vock et al. |
| 7,447,336 B2 | 11/2008 | Murakoshi et al. |
| 7,467,060 B2 | 12/2008 | Kulach et al. |
| 7,602,301 B1 | 10/2009 | Stirling et al. |
| 7,641,590 B2 | 1/2010 | Chan |
| 7,821,407 B2 | 10/2010 | Shears et al. |
| 7,825,815 B2 | 11/2010 | Shears et al. |
| 7,827,000 B2 | 11/2010 | Stirling et al. |
| 7,877,226 B2 | 1/2011 | Chan et al. |
| 7,889,085 B2 | 2/2011 | Downey et al. |
| 7,909,737 B2 | 3/2011 | Ellis et al. |
| 7,931,562 B2 | 4/2011 | Ellis et al. |
| 7,980,998 B2 | 7/2011 | Shemesh |
| 8,036,826 B2 | 10/2011 | MacIntosh et al. |
| 8,036,850 B2 | 10/2011 | Kulach et al. |
| 8,055,469 B2 | 11/2011 | Kulach et al. |
| 2010/0204952 A1 | 8/2010 | Irlam et al. |
| 2010/0210975 A1 | 8/2010 | Anthony, III et al. |
| 2011/0149694 A1* | 6/2011 | Sakita ............... A63B 69/12 368/10 |
| 2011/0153042 A1 | 6/2011 | Burton et al. |
| 2013/0259579 A1* | 10/2013 | Bonzon ............. B63C 11/2245 405/186 |

FOREIGN PATENT DOCUMENTS

| | | | |
|---|---|---|---|
| JP | 2007-229416 | 9/2007 | |
| WO | WO 8705229 A2 * | 9/1987 | ......... A63B 71/0686 |

\* cited by examiner

SWIM STROKE COUNTER

CROSS-REFERENCE TO RELATED PATENT APPLICATIONS

This patent application claims the benefit of U.S. Provisional Patent Application No. 61/731,182, filed Nov. 29, 2012, the entire teachings and disclosure of which are incorporated herein by reference thereto.

FIELD OF THE INVENTION

This invention generally relates to a system for detecting arm strokes or kick strokes (generically referred to as "strokes") by a swimmer.

BACKGROUND OF THE INVENTION

While diving and swimming a swimmer or diver (collectively referred to hereinafter as a "swimmer"), the swimmer will often track various information. For instance, swimmers who are diving may use a dive computer to track the amount of oxygen remaining in storage tanks, to measure the depth of the dive, the time of a dive, and to calculate and display an ascent profile to provide proper decompression.

Often, a swimmer is interested in the distance traveled and/or number of swimming strokes performed. The swimmer may also be interested in the kick efficiency.

Accurate distance measuring during diving and swimming interests many swimmers because of navigation. The simplest method is to count kick cycles. Further, a swimmer is interested in distance or stroke count done during exercise. When exercising at the pool, the counting of laps becomes difficult. Divers may train their kick technique by snorkel swimming.

Currently, accelerometers are used for determining swim strokes. Unfortunately, this requires the inclusion of additional sensors and gathering additional data to determine the number of swimming strokes performed by the swimmer.

The present invention provides improvements over the current state of the art relating to devices for identifying and analyzing swimming strokes by swimmers and divers. These and other advantages of the invention, as well as additional inventive features, will be apparent from the description of the invention provided herein.

BRIEF SUMMARY OF THE INVENTION

Embodiments of the present invention provide a new and improved stroke counter and method of determining strokes of a swimmer. More particularly, embodiments of the present invention sense changes in pressure proximate one or more extremities of a swimmer to determine individual strokes performed by the swimmer.

In a particular embodiment, stroke counter for use by a swimmer is provided. The stroke counter includes a pressure sensor and a processor configured to operably receive pressure information from the pressure sensor. The processor is configured to determine a stroke by analyzing the pressure information sensed by the pressure sensor.

In one embodiment, the pressure sensor and processor are formed as separate units that are operably coupled to one another to operably communicate the pressure information from the pressure sensor to the processor.

In on embodiment, the pressure sensor is configured to be operably attached proximate the swimmer's ankle and the processor is configured to be operably attached proximate the swimmer's arm. The pressure sensor and the processor may use separate straps for attaching the devices to the swimmer.

In one embodiment, the pressure sensor and processor are operably wirelessly coupled. Alternatively, they may be wired to one another.

In one embodiment, the pressure sensor and processor are positioned in a same housing.

In one embodiment, the system further includes a display for displaying information to the swimmer and particularly stroke information and/or estimated distance traveled.

In one embodiment, the processor is configured to analyze the pressure information and determine a stroke rate. In one embodiment, the processor is configured to determine an estimated swim distance by determining a number of strokes over a period of time and multiplying the number of strokes by a predetermined stroke distance value.

In one embodiment, the processor is configured to determine an estimated swim distance by determining a number of strokes over a period of time and multiplying the number of strokes by a selected stroke distance value. The processor contains at least two predetermined stroke distance values which may be stored in a data storage device of the processor. Each predetermined stroke value represents a different distance traveled per stroke identified. The processor is configured to be toggled between the at least two predetermined stroke distance values by the user such that different distances can be determined based on the predetermined stroke values. This allows for calibration for different travel distances per stroke by a diver at different styles of swimming, different rates of swimming, or for different simmers.

In one embodiment, the processor is configured to filter the pressure information to determine oscillations between high and low pressure to determine individual strokes.

In one embodiment, a display is operably coupled to the processor.

In one embodiment, a second pressure sensor is provided. The second pressure sensor is provided in a housing separate from the processor. This allows for pressure to be sensed at two separate locations such as proximate the feet and proximate the hands.

In one embodiment, the stroke counter is integrated to a dive computer and can operate also during diving. During immersion the stroke counter could be activated and used for distance counting.

When stroke counter is integrated into a dive computer, the stroke counting can be a selectable mode that the dive computer can automatically start and end based on an underlying dive mode when certain limits are met/exceeded. For instance, when the diver is three meters or less from the surface of the water, the dive computer could automatically switch from a diving mode to a stroke counting mode. Once the diver goes to a depth of greater than three meters, the dive computer may automatically switch to dive mode. When switching modes, the only change may be what information is displayed to the diver. However, the dive computer could continue to monitor and count strokes in the background.

Methods of analyzing strokes of a swimmer also provided. These methods may include determine when a diver performs a stroke either by kicking or using its arms.

The method includes sensing pressure proximate an extremity of a swimmer to generate pressure information and analyzing the pressure information to identify individual strokes of the swimmer.

In one embodiment, the method includes determining a stroke rate by analyzing the pressure information. In one embodiment, the method includes determining a total number strokes for a length of time.

In one embodiment, the step of sensing pressure proximate an extremity senses pressure proximate a hand of the swimmer. Alternatively, in one embodiment, the step of sensing pressure proximate an extremity senses pressure proximate a foot of the swimmer.

In one embodiment, the method includes determining a distance traveled by multiplying the number of strokes by a predetermined stroke distance.

In one embodiment, the step of sensing pressure proximate an extremity of a swimmer to generate pressure information includes sensing pressure information proximate an arm of the swimmer to gather a first set of pressure information relating to arm strokes of the swimmer and sensing pressure information proximate a leg of the swimmer to gather a second set of pressure information relating to kick strokes of the swimmer, the step of analyzing the pressure information includes analyzing the first set of pressure information to identify individual arm strokes and analyzing the second set of pressure information to identify individual kick strokes.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

Figure 1:
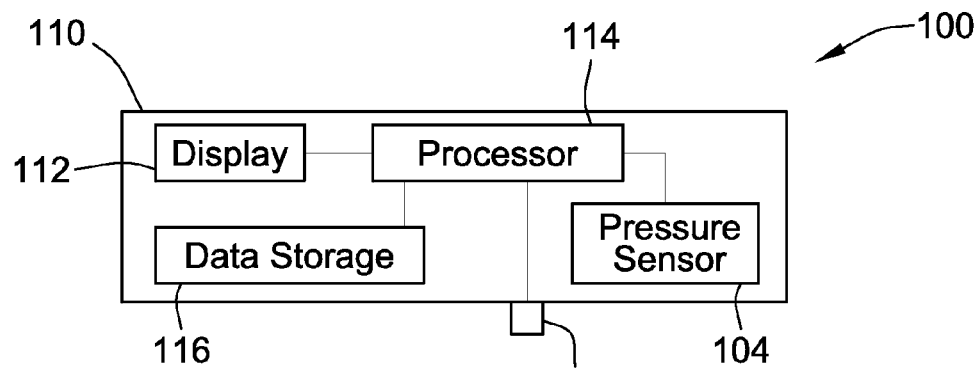
FIG. 1 is a simplified schematic illustration of a stroke counter in the form of a dive computer according to an embodiment of the invention.
Figure 2:
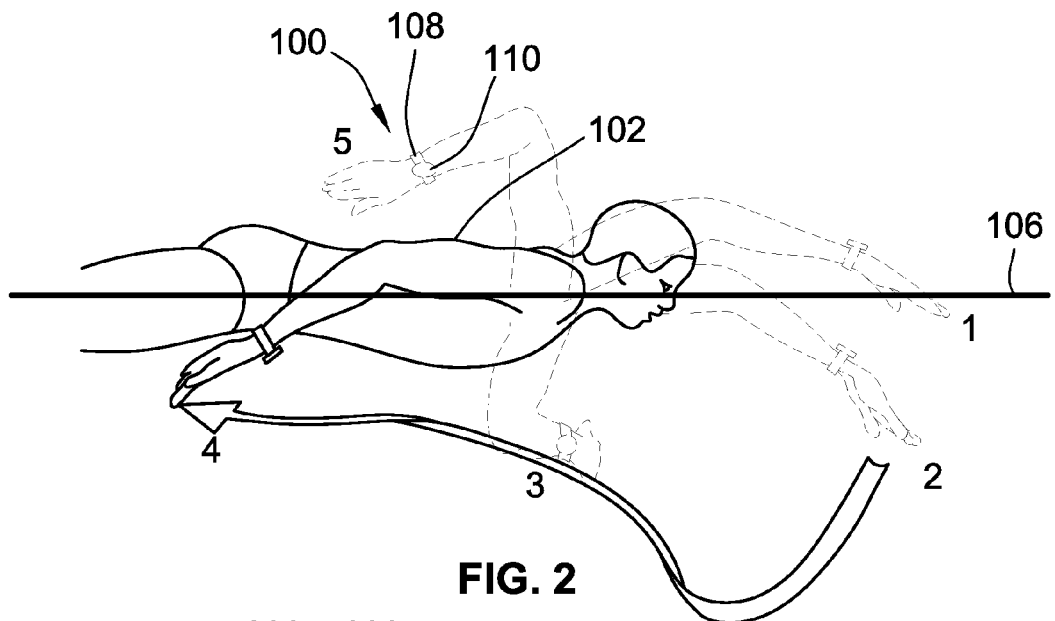
FIG. 2 is a schematic illustration of a swimmer and the arm strokes thereof while swimming at the surface of a body of water.

FIG. 1 illustrates a simplified embodiment of a stroke counter in the form of a dive computer 100 according to the present invention. The dive computer 100 is illustrated being worn on a wrist of a swimmer 102 in FIG. 2.

The dive computer 100 is used to count and/or keep track of the number of swimming strokes that the swimmer 102 performs. The dive computer 100 may be attached to the wrist of the swimmer 102 or the foot of the swimmer 102. This allows the swimmer 102 to track the number of arm strokes or kicks performed by the swimmer 102 over a period of time.

The dive computer 100 includes a pressure sensor 104 that detects pressure surrounding the dive computer 100. During cyclical arm or kicking strokes, a cyclical pattern of sensed pressure will emerge that can be analyzed to determine the number of arm or kick strokes so as to determine the number of swimming strokes performed by the swimmer 102.

While it is contemplated that the dive computer 100 can sense changes in pressure for various types of strokes, embodiments of the invention may find particular use when the swimmer 102 is swimming near or at the surface 106 of the water. This provides maximum pressure differential exposure when the pressure sensor 104 is repeatedly inserted into and removed from the water, such as during a typical free style stroke. In other words and in reference to FIG. 2, the pressure sensor 104 of the dive computer 100 senses the transition from the air to the surface of the water, through the initial downward pull of the stroke (the transition from location 1 to location 2), the vertically rising rearward portion of the stroke (the transition from location 2 to location 4 in FIG. 2), and the removal of the dive computer 100 from the water into the air at the end of the stroke cycle (the transition from location 4 to location 5 in FIG. 2). This repeated cycle can be analyzed to determine each individual stroke.

Figure 4:
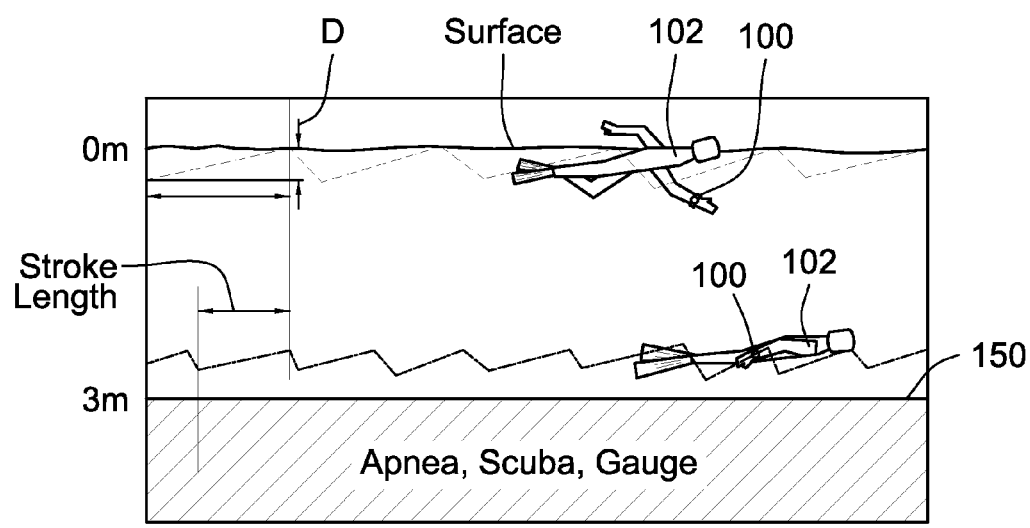
FIG. 4 is a simplified schematic illustration illustrating a desired depth of a stroke as well as a potential mode change over depth when the dive computer could switch from stroke counting to a diving mode.

Even when the dive computer 100 remains fully submerged, dive computer 100 can still perform stroke counting functions. For instance, if a sufficient change in depth occurs during strokes, the cyclical changes in pressure can be analyzed to determine strokes. This change in depth is illustrated in FIG. 4 by reference character D. It is preferred that each stroke where the pressure values are sensed has a change in depth D of greater than 8 centimeters and more preferably greater than 10 centimeters so as to have sufficient resolution between high and low pressure values. However, depending on the sensitivity of the pressure sensor 104, smaller changes in depth D may be used.

The dive computer 100 includes attachment structure in the form of a wrist band 108 for operably securing the dive computer 100 proximate to the extremities (i.e. at the wrist or ankle) of the swimmer 102. Other attachment structure can be used to operably secure the dive computer 100 to or proximate the extremities of the swimmer 102.

The dive computer 100 includes a waterproof housing 110 to which the wrist band 108 is operably secured.

The dive computer 100 further includes a visual display 112 configured to display information to the swimmer 100. This information may include the number of strokes performed, an estimated distance traveled, a stroke rate, as well as other information such as information relating to diving. The display may be a fixed display with predetermined fixed information that is displayed to the swimmer or an adjustable display where the swimmer 100 can define which information is displayed and how the information is organized or configured.

The dive computer 100 includes a processor 114 that operably receives the pressure information sensed from the pressure sensor 104. In the embodiment of FIG. 1, the pressure sensor 104 is operably coupled to the processor 114 by appropriate circuitry and wiring to supply the pressure information to the processor 114. The processor 114 can use numerous methods for analyzing the pressure data to determine the number of strokes. For instance, in one embodiment, the processor could identify a stroke each time a predetermined pressure difference is identified. In this embodiment, both the processor 114 and pressure sensor 110 are positioned within or otherwise operably supported by housing 110.

The processor 114 may also determine the individual strokes based on a predetermined pressure value that can be given by the user. This pressure value could be given in form of depth by the swimmer 102 which can be correlated to a predetermined pressure value for simple configuration/calibration of the dive computer 100. In some embodiments, a high pressure and low pressure value could be input and each time a set of data including a high pressure value and a low pressure value is recorded, a single stroke could be determined. These set point values can be stored in the data storage unit 116. The depth value or differential of the stroke can be altered when, for example, different fins are used. This allows the diver or swimmer to compensate for the size of the fin blades because small blades allow larger stroke amplitude, which results in larger differential pressure values.

The processor 114 can also determine an estimated distance traveled. To do this, the swimmer 102 would set a distance traveled per stroke. This could be manually entered into the dive computer 100 and stored in data storage unit 116. Typically, the distance traveled per stroke would be determined by the swimmer 102 when swimming in predefined conditions such as a pool. This could be done using a menu programmed into the processor. The processor 114 would then multiply the number of strokes performed by the predetermined distance traveled per stroke. Further, the dive computer 100 could be programmed with different stroke distance values based on any one of the following characteristics such as height, age, swimming levels (i.e. beginner, intermediate, expert), or swim stroke type (i.e. freestyle, with kicking, without kicking, etc.). This information would be stored in the data storage unit 116.

The processor 114 will typically use filtering techniques to filter the pressure information so as to make it easier to analyze when swimming strokes occur.

The dive computer 100 can include one or more buttons 118 used to activate the stroke counting function or to toggle between information that is displayed on display 112.

The dive computer 100 can be used to discern a kick cycle as well. To analyze kick information of a swimmer, the dive computer 100 must be attached proximate the foot, typically at the ankle, of the diver 102. As the ankle is repeatedly lifted up and out of the water and stroked down and into the water for each kick cycle, the pressure can be sampled by the pressure sensor 104 just like discussed above.

While the prior embodiment discusses the use of a dive computer. The system could be embodied in a unit that does not include all of the functionality of a dive computer.

When stroke counter is integrated into a dive computer such as dive computer 100, the stroke counting can be a selectable mode that the dive computer 100 can automatically start and end based on an underlying dive mode when certain limits are met/exceeded. With reference to FIG. 4 for instance, when the diver 102 is three meters or less from the surface 106 of the water, i.e. above mode threshold 150, the dive computer 100 could automatically switch to a stroke counting mode, such as from a diving mode. Once the diver 102 goes to a depth of greater than three meters, i.e. below mode threshold 150, the dive computer 100 may automatically switch to dive mode. This can be detected based on the pressure date that is sampled by the dive computer 100. When switching modes, the only change may be the information that is displayed to the diver 102. However, the dive computer 102 could continue to monitor and count strokes in the background. Embodiments of the invention therefore include this ability to switch between different modes.

Figure 3:
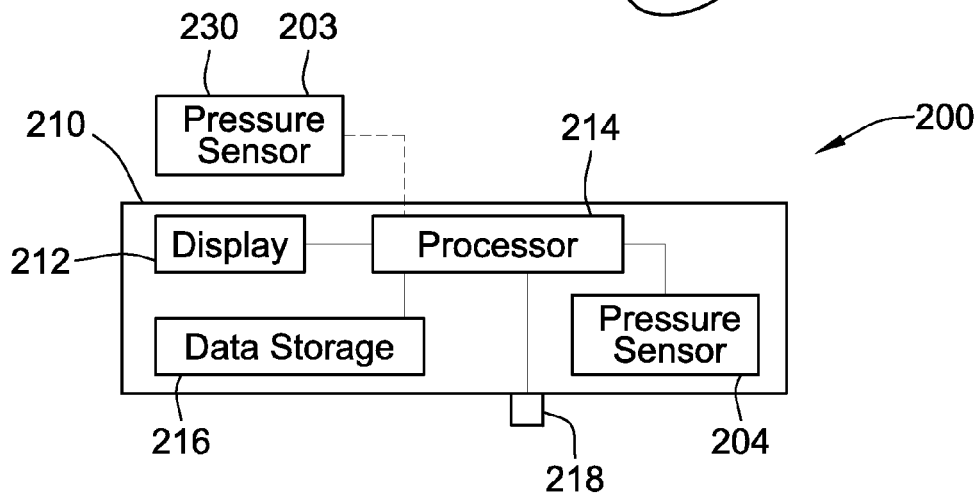
FIG. 3 is a simplified schematic illustration of a second embodiment of a stroke counter that includes a dive computer and an independent pressure sensor that is physically separate from the dive computer.

FIG. 3 is a simplified illustration of a second embodiment of a stroke counter 201 that includes a dive computer 200 and an independent pressure sensor 203. This embodiment eliminates the problem with the prior embodiment in that the swimmer 102 is unable to read the display 112 of the dive computer 100 if it is attached to the swimmer's foot/ankle.

This stroke counter 201 allows the independent pressure sensor 203 to be separately attachable to the swimmer 102 and particularly to its ankle while the dive computer 200 is attached to the wrist of the swimmer 102. Thus, the pressure information that is sampled by the independent pressure sensor 203 can be sampled proximate the foot of the swimmer 102 while the display 212 of the dive computer 200 is still visible to the swimmer 102 during swimming or diving activities.

The dive computer 200 may be substantially identical to dive computer 100 of the prior embodiment and will typically include a display 212, processor 214, data storage 216, housing 210 and buttons 218. The stroke counter 201 also includes a pressure sensor 204 positioned within housing 210. As such, in this embodiment, both arm stroke and kick stroke information can be gathered and analyzed. Alternative embodiments may not include pressure sensor 204.

The pressure sensor 203 may be wired to the dive computer 210 or connected to the dive computer 210 and operably connected to processor 214 using wireless technology. The pressure sensor 203 preferably includes a separate housing 230 such that it is a self-contained unit that is independent from dive computer 200 which is in the form of its own self-contained unit. In such embodiment, motion of the pressure sensor 203 can be entirely independent of motion of dive computer 200. As such, if the swimmer 102 is only kicking and not using his or her arms, such as if he or she is snorkeling, kick stroke information will be gathered. If the swimmer 102 then begins to use his or her arms, the arm stroke information will begin to be gathered.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A stroke counter for use by a swimmer, comprising:
    a pressure sensor;
    a processor receiving pressure information from the pressure sensor, the processor configured to determine a stroke by analyzing the pressure information sensed by the pressure sensor, the processor also configured to determine a depth of the swimmer by analyzing the pressure information sensed by the pressure sensor;
    an attachment structure for attaching the stroke counter to one of a hand of the swimmer to sense a pressure proximate the hand of the swimmer or a foot of the swimmer to sense a pressure proximate the foot of the swimmer; and
    wherein the processor is configured to automatically switch between a stroke counting mode and a dive mode based on the pressure information collected by the pressure sensor.

2. The stroke counter of claim 1, wherein the pressure sensor and processor are formed as separate units that are operably coupled to one another to operably communicate the pressure information from the pressure sensor to the processor.

3. The stroke counter of claim 2, wherein the pressure sensor is configured to be operably attached proximate the swimmer's ankle and the processor is configured to be operably attached proximate the swimmer's arm.

4. The stroke counter of claim 3, wherein the pressure sensor and processor are operably wirelessly coupled.

5. The stroke counter of claim 1, wherein the pressure sensor and processor are positioned in a same housing.

6. The stroke counter of claim 1, wherein the processor is configured to analyze the pressure information and determine a stroke rate.

7. The stroke counter of claim 1, wherein the processor is configured to determine an estimated swim distance by determining a number of strokes over a length of time and multiplying the number of strokes by a predetermined stroke distance value.

8. The stroke counter of claim 1, wherein the processor is configured to determine an estimated swim distance by determining a number of strokes over a length of time and multiplying the number of strokes by a selected stroke distance value, the processor contains at least two predetermined stroke distance values, each predetermined stroke value representing a different distance traveled per stroke, the processor is configured to be toggled between the at least two predetermined stroke distance values by the user such that different distances can be determined based on the predetermined stroke values.

9. The stroke counter of claim 1, wherein the processor is configured to filter the pressure information to determine oscillations between high and low pressure to determine individual strokes.

10. The stroke counter of claim 1, further comprising a display operably coupled to the processor, the display is configured to display information relating to the strokes of the swimmer.

11. The stroke counter of claim 1, further comprising a second pressure sensor, the second pressure sensor provided in a housing separate from the processor.

12. The stroke counter of claim 1, wherein the processor is configured to automatically switch between the stroke counting mode and the dive mode at a predetermined depth of the swimmer based on the pressure information collected by the pressure sensor.

13. The stroke counter of claim 12, further comprising a display operably coupled to the processor, the display is configured to display information relating to the strokes of the swimmer, and wherein the processor is configured to change the information displayed on the display when automatically switching between the stroke counting mode and the dive mode.

14. A method of analyzing strokes of a swimmer, comprising:
    sensing, with a pressure sensor, a pressure proximate an extremity of a swimmer to generate pressure information, wherein the step of sensing pressure proximate an extremity senses pressure proximate one of a hand of the swimmer or a foot of the swimmer;
    analyzing the pressure information to identify individual strokes of the swimmer and to identify a depth of the swimmer with a processor; and
    further comprising automatically switching between a stroke counting mode and a dive mode based on the step of analyzing the pressure information.

15. The method of claim 14, further comprising determining a stroke rate by analyzing the pressure information.

16. The method of claim 14, further comprising determining a total number strokes for a length of time.

17. The method of claim 16, further comprising determining a distance traveled by multiplying the number of strokes by a predetermined stroke distance.

18. The method of claim 14, wherein sensing pressure proximate an extremity of a swimmer to generate pressure information includes sensing pressure information proximate an arm of the swimmer to gather a first set of pressure information relating to arm strokes of the swimmer and sensing pressure information proximate a leg of the swimmer to gather a second set of pressure information relating to kick strokes of the swimmer, the step of analyzing the pressure information includes analyzing the first set of pressure information to identify individual arm strokes and analyzing the second set of pressure information to identify individual kick strokes.

19. The method of claim 14, wherein analyzing the pressure information includes analyzing a cyclical pattern of the sensed pressure to identify individual strokes of the swimmer.

20. The method of claim 19, further comprising identifying an individual stroke with each peak or valley of the cyclical pattern.

21. The method of claim 14, wherein automatically switching between a stroke counting mode and a dive mode includes changing information displayed to the swimmer.

22. The method of claim 14, wherein automatically switching between a stroke counting mode and a dive mode includes continuing to identify individual strokes of the swimmer.

23. The method of claim 14, wherein automatically switching between a stroke counting mode and a dive mode includes switching at a predetermined depth of the swimmer.

24. A stroke counter for use by a swimmer, comprising:
a pressure sensor;
a processor receiving pressure information from the pressure sensor, the processor configured to determine a stroke by analyzing the pressure information sensed by the pressure sensor, the processor is configured to automatically switch between a stroke counting mode and a dive mode based on the pressure information collected by the pressure sensor; and
an attachment structure for attaching the stroke counter to the swimmer at a point of attachment to sense a pressure proximate the point of attachment.

25. The stroke counter of claim 24, wherein the processor is configured to automatically switch between the stroke counting mode and the dive mode at a predetermined depth of the swimmer based on the pressure information collected by the pressure sensor.

26. The stroke counter of claim 24, further comprising a display operably coupled to the processor, the display is configured to display information relating to the strokes of the swimmer, and wherein the processor is configured to change the information displayed on the display when automatically switching between the stroke counting mode and the dive mode.

* * * * *